United States Patent [19]

Engelhardt et al.

[11] Patent Number: 4,917,530

[45] Date of Patent: Apr. 17, 1990

[54] STRUCTURAL JOINT

[75] Inventors: John A. Engelhardt, Warsaw; David C. Kelman, Winona Lake, both of Ind.

[73] Assignee: Boehringer Mannheim Corporation, Indianapolis, Ind.

[21] Appl. No.: 401,178

[22] Filed: Aug. 31, 1989

[51] Int. Cl.[4] .............................................. B25G 3/00
[52] U.S. Cl. ..................................... 403/334; 403/41; 403/361
[58] Field of Search ................ 403/333, 334, 41, 268, 403/361

[56] References Cited

U.S. PATENT DOCUMENTS

| | | |
|---|---|---|
| 1,896,261 | 2/1933 | True . |
| 2,331,020 | 10/1943 | Frances . |
| 2,795,440 | 6/1957 | Holycross et al. . |
| 3,264,012 | 8/1966 | Giovanazzi et al. . |
| 3,494,642 | 2/1970 | Coberly et al. . |
| 3,655,244 | 4/1972 | Swisher . |
| 4,653,953 | 3/1987 | Anderson et al. ................. 403/41 X |
| 4,692,057 | 9/1987 | Lauderbach ........................ 403/334 |

Primary Examiner—Andrew V. Kundrat
Attorney, Agent, or Firm—Perman & Green

[57] ABSTRACT

A structural joint which may be for orthopedic use is effective to simultaneously resist bending and torsional loading. It includes a female member formed with a cone shaped bore and a mouth defining entry into the bore. A male member matingly engageable with the female member has a contoured outer surface which includes a coupling element sized and shaped for mating engagement with the bore. When the male and female members are joined, the coupling element extends to a location within the bore spaced from the mouth and joins, via a smooth surfaced intermediate element, to a transitional element whose transverse dimension is substantially smaller than the mouth of the bore as it extends through and beyond the mouth. The bore and the coupling element may be mutually tapered such that the male and female members become locked together when engaged.

6 Claims, 1 Drawing Sheet

STRUCTURAL JOINT

BACKGROUND OF THE INVENTION

1. Field of the Invention

The present invention relates generally to structural joints and, more particularly, to a structural joint of the tapered variety which is especially effective when subjected to bending stresses.

2. Description of the Prior Art

The joining together of structural members such that the members experience minimal relative motion when subjected to loading is a classic and perplexing problem. Many methods and constructions have been explored in attempts to solve to the problem. Among them are screw threads, including the modern spiral lock type, and the locking taper.

The locking taper was initially designed to join rotating elements and is used in many applications including aerospace, automotive and general machinery. Conventional locking tapers are of three main types, namely, Morse, Brown and Sharpe, and Jarno. The major difference between these types of tapers is the angle of the mated tapered cones. It is generally considered that a set of cones is of the locking type when the included angle is less than 6 degrees. The locking taper provides limited resistance to torsion, bending, and distraction of the components it joins, and is ideally suited for rotating spindles experiencing moderate side loading.

However when bending is the predominant mode of loading, certain problems arise with the use of conventional locking tapers. Specifically when a bending moment is imparted to the system, deflection of the components causes impingement of the male member against the female member at the mouth of the female member. This impingement causes a point loading stress concentration combined with the adverse effects of relative motion and resultant wear when subjected to cyclic bending. If material is removed from the male member to accommodate this condition, the section modulus decreases and localized stresses increase to the point of failure.

One obvious solution is to flare the mouth of the female portion such that impingement of the male member against the female member never occurs at that location. Of course, this is only possible when the female member is of sufficient size to accommodate formation of a flare. This solution is also impractical insofar as it is rather difficult to manufacture.

The prior art includes numerous examples of tapered joints. Many of them relate to tubes and pipes and attempts to seal the tubes and pipes against leakage. Typical of such constructions are the U.S. Patents to Handa et al., No. 4,623,173; to Saunders et al., No. 4,549,754; to Coberly et al., No. 3,494,642; to Giovanazzi et al., No. 3,264,012; to Holycross et al., No. 2,795,440; to Frances, No. 2,331,020; and to True, No. 1,896,261.

A different mode of construction is presented in the patent to Holycross et al, No. 2,795,440. While stress relief of the joint is said to be of concern, the subject of the Holycross et al invention is tubular in its configuration and relates to a concentric chamfer to provide increased volume to receive cement used for sealing purposes.

U.S. Pat. No. 3,655,244 discloses a percussion tool which utilizes a recessed end for mating reception of a tool element. Mating surfaces of the recessed end and of the tool element are mathematically generated to assure ease of initial installation and subsequent removal of the tool element.

Unfortunately, none of the foregoing known constructions provides a solid joint which can be readily assembled and disassembled, is capable of withstanding extreme stresses in torsion, compression, and bending as well as intermittent and shock loading of the type which is imparted when the joint is used, for example, in a prosthetic manner in the human body.

SUMMARY OF THE INVENTION

It was in light of the deficiencies existing in the prior art just described that the present invention was conceived and has now been reduced to practice. To this end, a structural joint has been devised which is effective to simultaneously resist bending, compression, and torsional loading. It includes a female member formed with a cone shaped bore and a mouth defining entry into the bore. A male member matingly engageable with the female member has a contoured outer surface which includes a coupling element sized and shaped for mating engagement with the bore. When the male and female members are joined, the coupling element extends to a location within the bore spaced from the mouth and joins, via a smooth surfaced intermediate element, to a transitional element whose transverse dimension is substantially smaller than the mouth of the bore as it extends through and beyond the mouth. The bore and the coupling element may be mutually tapered such that the male and female members become locked together when engaged.

As a result of this construction, impingement of the male member against the mouth of the female member is prevented. Furthermore, this result is achieved without otherwise compromising the benefits provided by the tapered joint construction.

While the invention has particular application to a joint designed with a locking taper, it is just as applicable to tapered joints not of the locking variety.

An additional feature of the invention resides in the fact that it can be readily fabricated using existing materials and machinery.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and, together with the description, serve to explain the principles of the invention in general terms. Like numerals refer to like parts throughout the disclosure.

DETAILED DESCRIPTION OF THE PREFERRED EMBODIMENT

Figure 1:
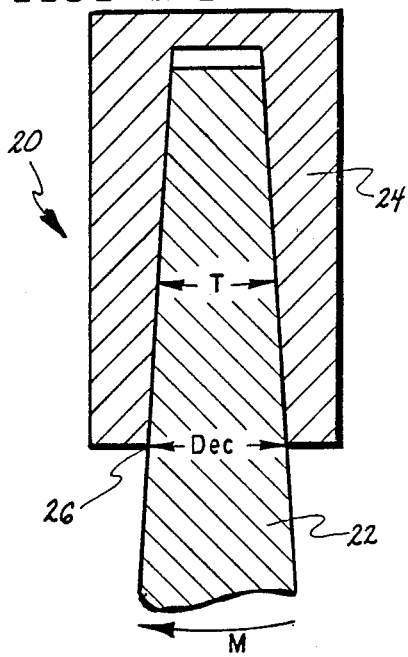
FIG. 1 is a detail view of a prior art construction of a tapered structural joint illustrated in cross section in which a male member is engaged with a female member.

Turn now to the drawings and, initially, to FIG. 1 which illustrates a conventional tapered structural joint 20 in which a male member 22 is engaged with a female member 24. The structural joint 20 may or may not be a locking taper. It is generally considered that a locking taper is one in which the included angle T (FIG. 1) is less than 6°. When a bending moment, M (FIG. 1) is imparted to the structural joint 20, deflection of the male member 22 causes impingement at location 26 at the mouth or entry into the female member This impingement causes a point loading stress concentration and subsequent relative motion and accompanying wear of the female member 24 and of the male member 22 when the structural joint is subjected to cyclic bending. In time, the male member 22 becomes worn at the impingement location, reducing its section modulus, with a resultant localized stress increase until, eventually, failure occurs. By the same token, wear, cracking, and possible disintegration of the female member 24 may also occur, rendering the structural joint ineffective.

Figure 2:
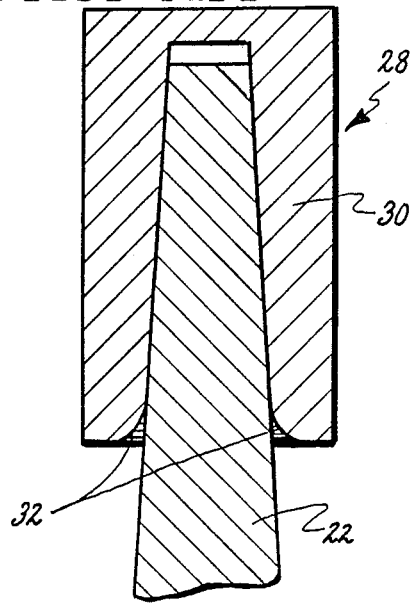
FIG. 2 is a prior art construction of a tapered structural joint, similar to FIG. 1, in which the mouth into the female member is flared in an attempt to accommodate bending movement of the male member.

In FIG. 2, a modified structural joint 28 is depicted which provides an obvious solution to some of the difficulties which have just been described with respect to the FIG. 1 construction. In this instance, a female member 30 has been modified so as to provide a flared opening 32 into the interior of the female member. While this construction reduces the possibility of impingement which occurs at location 26 in the FIG. 1 construction, it is an impractical solution in actual practice since the female member 24 must be sufficiently large to accommodate the flared opening 32. Even more pertinent, however, is the fact that the flared opening 32 is difficult and expensive to manufacture, particularly when large quantities of the joint are required.

Figure 3:
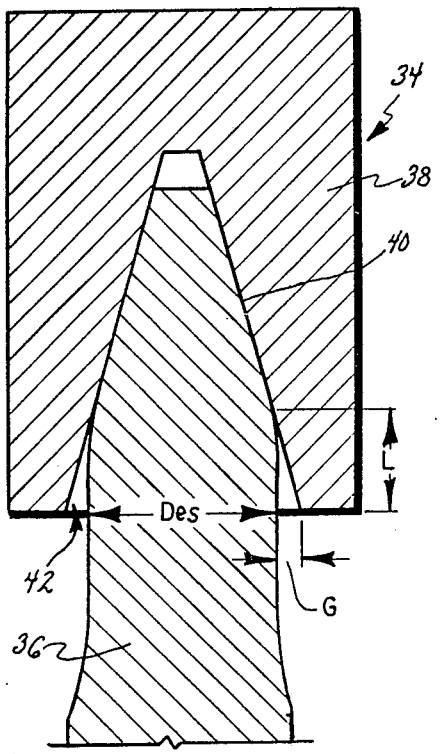
FIG. 3 is a detail cross section view depicting a modified tapered structural joint embodying the invention.
Figure 4:
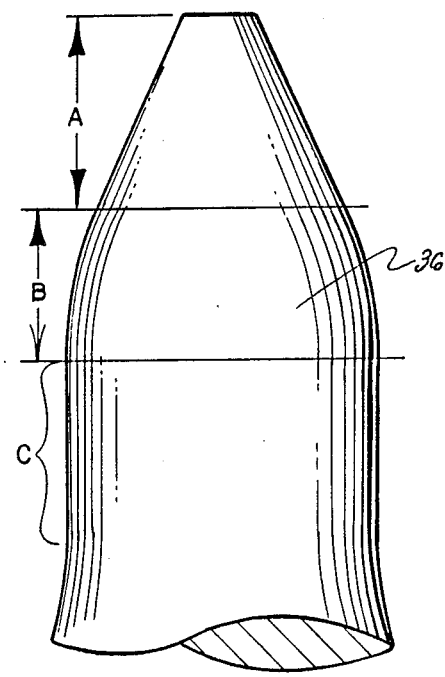
FIG. 4 is a detail side elevation view, exaggerated, of the male member of the tapered structural joint depicted in FIG. 3.

The construction illustrated in FIGS. 3 and 4 provides an easily manufacturable solution to the problem posed by the conventional structural joints 20 and 28, particularly when they are subjected to severe cyclic bending forces. As illustrated in FIGS. 3 and 4, the novel structural joint 34 includes mating male and female members 36 and 38, respectively, shown operatively engaged. The female member 38 is substantially similar to the female member 24 of the FIG. 1 embodiment. In this regard, the female member 38 has a bore 40 which is shaped as a right circular cone with a mouth 42 defining entry into the bore.

According to the invention, only the male member 36 is modified, as compared with the FIG. 1 and 2 prior art constructions, so as to be prevented from impinging upon the female member 38 when subjected to stresses which cause its deflection. Indeed, the male member 36 is designed to assure that impingement never occurs at the mouth 42 regardless of the stresses imposed on the male member.

As previously explained, FIG. 4 illustrates the male member 36 in a highly exaggerated form. As seen in FIG. 4, reference symbol A represents that portion of the male member 36 which is a right circular cone and intended for contiguous mating engagement with the bore 40 as seen in FIG. 3. Reference symbol C represents that portion of the male member 36 which is a right circular cylinder. When the male member 36 is joined with the female member 38 as seen in FIG. 3, the portion C traverses the mouth 42. That is, the cylindrical portion C both extends into the bore 40 and outside of or beyond the female member 38 by a substantial distance in each direction. Reference symbol B represents that portion of the male member 36 which has a smooth continuous curving outer surface interconnecting the portion A and the portion C. Indeed, the portion B blends into the portion A preferably in a tangential manner as it does also with the portion C. The portion B may be shaped as an arc of a circle, as an ellipse, as a compound curve, or preferably as a parabola, or be of any other suitable shape which is continuous and smooth so as to rollingly engage the bore 40.

When the male and female members 36, 38, respectively, are assembled as seen in FIG. 3, the diameter of the mouth 42 is such that a gap G is provided. The gap G is of a sufficient dimension to assure that the deflection of the male member 36 under normal, or even excessive, loading is less than the value G. In this manner, the design of the invention assures that an impingement stress concentration does not occur at the mouth 42. It is worthwhile to note that the exit diameter of the male member 36, that is, its diameter $D_{es}$ in the portion C (FIG. 3), is less than the exit diameter $D_{ec}$ of the conventional male member 22 (see FIG. 1). This is by virtue of the novel design of the invention. Indeed, the obvious solution to the problem would be achieved by increasing the diameter $D_{ec}$ while the solution provided by the invention is achieved by reducing the diameter of the male member 36 to $D_{es}$.

However, it will be appreciated that not just any reduction of the diameter of the male member 36 will suffice for purposes of the invention. Indeed, it is important to note that there is a moderately well defined "window" of relative dimensions of the components which will achieve the goals of the invention and that dimensions lying outside of that window will be unsatisfactory. Thus some reduction of the diameter $D_{es}$ with concomitant increase in the dimension of the gap G is beneficial to avoid impingement of the male member 22 on the mouth 42. Nonetheless, if the diameter $D_{es}$ is too small, the male member will be able to deflect to the extent that it impinges on the mouth 42.

A structural joint formed in accordance with the invention achieves its maximum strength when the following mathematical relationship is satisfied:

$$KS_c > S_s$$

Where $S_c$ is the calculated stress adjacent location 26 in the conventional tapered male component;

$S_s$ is the calculated stress adjacent mouth 42 in the tapered male component modified in accordance with the invention; and K is the Stress concentration of the conventional component due to impingement at the location 26.

EXAMPLE

While a structural joint composed of numerous different materials and having a variety of different dimensions can satisfy the goals of the invention, such a joint having the following characteristics has been fabricated and determined to be acceptable:

L=0.20 inches where L is the distance from the line of tangency to the mouth 42 (FIG. 3)

$G = 4.2 \times 10^{-3}$ *inches*
$D_{es} = 570.6 \times 10^{-3}$ *inches*
*Diameter of mouth* 42 $= 579.0 \times 10^{-3}$ *inches*
Material: Ti-6A1-4V The structural joint of the invention thus assures that minimal relative motion occurs between the male and female components when subjected to severe cyclic bending while maintaining resistance to compression, distraction and rotational forces. The concept presented is furthermore highly practical in that it is of a design which can be readily manufactured.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A structural joint comprising:
   a female member having an elongated generally right circular cone shaped bore therein with a mouth defining entry into the bore; and
   an elongated male member matingly engageable with said female member having a contoured outer surface extending between a terminal end and an inboard region, said male member including:
   a generally right circular cone shaped coupling element adjacent said terminal end congruently sized and shaped relative to the bore in said female member for mating engagement with the bore and, when joined with said female member, extends to a location within the bore spaced from the mouth thereof;
   a transitional element having a transverse dimension substantially smaller than the mouth of the bore extending longitudinally of said male member from a location within the bore spaced from the mouth thereof to a location beyond the mouth of the bore when said male member is joined with said female member; and
   an intermediate element having a smooth convex shaped outer surface of continuous curvature interconnecting said coupling element and said transitional element such that upon the application of bending stresses on said male member, said convex shaped outer surface of said intermediate element is caused to rollingly engage the bore of said female member.

2. A structural joint as set forth in claim 1 wherein said coupling element of said male member and the bore of said female member each has a longitudinal axis and a taper angle of less than 6° relative to its associated longitudinal axis.

3. A structural joint as set forth in claim 1 wherein each of said coupling element of said male member and the bore of said female member has a taper angle such that said male member and said female member become locked together when joined.

4. A structural joint as set forth in claim 1 wherein the mouth defining entry into the bore is circular; and
   wherein said transitional element is a right circular cylinder.

5. A structural joint as set forth in claim 1 wherein both said female member and said male member are composed of solid material.

6. A structural joint for a prosthesis intended for implantation in a body comprising:
   a female member adapted to be implanted in a bone, said female member having an elongated generally right circular cone shaped bore therein with a mouth defining entry into the bore; and
   an elongated male member matingly engageable with said female member having a contoured outer surface extending between a terminal end and an inboard region, said male member including:
   a generally right circular cone shaped coupling element adjacent said terminal end congruently sized and shaped relative to the bore in said female member for mating engagement with the bore and, when joined with said female member, extends to a location within the bore spaced from the mouth thereof;
   a transitional element having a transverse dimension substantially smaller than the mouth of the bore extending longitudinally of said male member from a location within the bore spaced from the mouth thereof to a location beyond the mouth of the bore when said male member is joined with said female member; and
   an intermediate element having a smooth convex shaped outer surface of continuous curvature interconnecting said coupling element and said transitional element such that upon the application of bending stresses on said male member, said convex shaped outer surface of said intermediate element is caused to rollingly engage the bore of said female member.

* * * * *